United States Patent

Maruyama et al.

Patent Number: 5,892,099
Date of Patent: Apr. 6, 1999

[54] 3,7-DITHIAPROSTANOIC ACID DERIVATIVE

[75] Inventors: Toru Maruyama; Shuichi Ohuchida, both of Osaka, Japan

[73] Assignee: Ono Pharmaceutical Co., Ltd., Osaka, Japan

[21] Appl. No.: 13,885

[22] Filed: Jan. 27, 1998

[30] Foreign Application Priority Data

Jan. 27, 1997 [JP] Japan ..................................... 9-027198

[51] Int. Cl.[6] .................................................. C07C 177/00
[52] U.S. Cl. ............................ 560/121; 560/15; 562/503; 562/426; 514/573; 514/530
[58] Field of Search ..................... 560/121, 15; 562/503, 562/426; 514/573, 530

[56] References Cited

FOREIGN PATENT DOCUMENTS 57-108065  7/1982  Japan .
58-110562  7/1983  Japan .
58-148857  9/1983  Japan .

*Primary Examiner*—Paul J. Killos
*Attorney, Agent, or Firm*—Stevens, Davis, Miller & Mosher, L.L.P.

[57] ABSTRACT

A 3,7-dithiaprostanoic acid derivative of the formula (I)

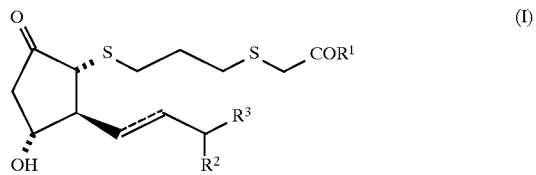

(wherein $R^1$ is OH, C1–4 alkoxy, $NR^6R^7$ (wherein $R^6$, $R^7$ are H, C1–4);$R^2$ is H, OH; $R^3$ is (i)alkyl, alkenyl, alkynyl (ii) phenyl, cycloalkyl (iii) alkyl, alkenyl, alkynyl substituted by phenyl, cycloalkyl (when $R^2$ is H, alkyl, alkenyl, alkynyl in (i) or (iii) may be substituted by OH) possesses a binding activity for $PGE_2$ receptor (especially for EP4). Therefore they are useful for the treatment and/or prevention of immunologic diseases (autoimmune diseases, immunological deficiency diseases, organ transplantation etc.), asthma, abnormal bone formation, neuronal cell death, liver damage, nephritis, hypertension, myocardiac ischemia etc.

12 Claims, No Drawings

3,7-DITHIAPROSTANOIC ACID DERIVATIVE

SUMMARY

The present invention provides 3,7-dithiaprostanoic acid derivatives. More particularly, the present invention provides:

1) a 3,7-dithiaprostanoic acid derivative of formula (I):

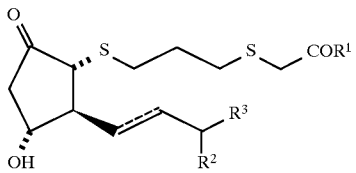

(wherein all symbols are the same meaning as defined hereafter)

2) processes for the preparation of them and 3) pharmaceutical compositions containing them.

BACKGROUND

Prostaglandin E$_2$ (abbreviated as PGE$_2$ hereafter) has been known as a metabolite in the arachidonate cascade. Its known activities include cyto-protective activity, uterine contractile activity, a pain-inducing effect, a promoting effect on digestive peristalsis, an awakening effect, a suppressive effect on gastric acid secretion, hypotensive activity and diuretic activity etc. In recent study, it was found that PGE2 receptor was divided into some subtypes which possess different physiological role from each other. At present, four receptor subtypes are known and they are called EP1, EP2, EP3 and EP4 (Negishi M. et al, J. Lipid Mediators Cell Signalling 12, 379–391 (1995) ).

The present inventors investigated to find compounds which bind to each receptor specifically; we found that the compounds of the present invention could bind strongly to EP4 subtype receptor and then achieved the present invention.

The compound of formula (I) possess a binding activity for EP4 subtype receptor strongly. Therefore they are useful for the treatment and/or prevention of immunologic diseases (autoimmune diseases, immunological deficiency diseases, organ transplantation etc.), asthma, abnormal bone formation, neuronal cell death, liver damage, nephritis, hypertension, myocardiac ischemia etc.

Among the compounds of the present invention of the formula (I), compounds which bind weakly to receptor subtypes except for EP4 receptors do not express other effects and therefore it is thought that such compounds will be a medical agent which have less side-effects.

On the other hand, many modified PGs wherein 7th position carbon atom is replaced by sulfur atom are known. The following application is mentioned for an example.

In the specification of Japanese Kokai No. 57-108065 (i.e. EP 51284), the following compounds are disclosed as an agent for anti-platelets aggregation.

I.e. 7-thiaprostaglandin derivatives of the formula (A):

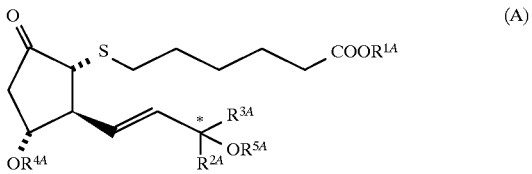

(wherein $R^{1A}$ is hydrogen atom, lower alkyl or pharmaceutically acceptable cation,
$R^{2A}$ is hydrogen atom or methyl,
$R^{3A}$ is C5–7 alkyl or cycloalkyl,
$R^{4A}$ and $R^{5A}$ is hydrogen atom or a protective group for hydroxy. Symbol * means the existence of an asymmetric carbon, its stereo configuration is α, β or a mixture thereof in voluntary ratio).

In the specification of Japanese Kokai No. 58-148857, the following compounds are disclosed as an agent for anti-platelet aggregation.

I.e. 7-thiaprostaglandin derivatives of the formula (B):

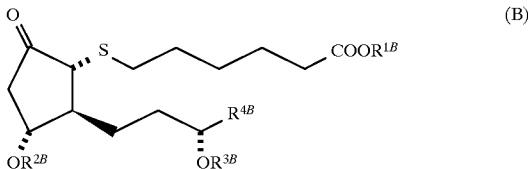

(wherein $R^{1B}$ is hydrogen atom or C1–10 alkyl, 5–6 membered alicyclic ring or phenyl,
$R^{2B}$ and $R^{3B}$ are, same or different, hydrogen atom, tri(C1–C8)hydrocarbon-silyl or a group capable to form acetal together with oxygen atom of hydroxy,
$R^{4B}$ is C3–C8 alkyl or 5–6 membered alicyclic ring).

In the specification of Japanese Kokai No. 58-110562, it is disclosed that the following compounds are useful for controlling vascular action.

I.e. 7-thiaprostaglandin derivatives of the formula (C):

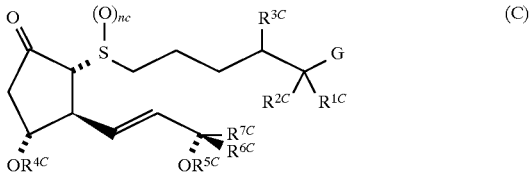

(wherein G is —COOR$^{8C}$, —CONR$^{9C}$R$^{10C}$ or —CH$_2$OR$^{11C}$,
wherein R$^{8C}$ is hydrogen atom, C1–C10 alkyl, substituted or unsubstituted phenyl, substituted or unsubstituted alicyclic ring, substituted or unsubstituted phenyl (C1–C3)alkyl or one equivalent weight cation,
R$^{9C}$ and R$^{10}$C, same or different, are hydrogen atom, C1–C10 alkyl, substituted or unsubstituted C5–C8 alicyclic ring, substituted or unsubstituted phenyl, substituted or unsubstituted alicyclic ring or substituted or unsubstituted phenyl(C1–C3)alkyl.
R$^{9C}$ and R$^{10C}$ may be form a substituted or unsubstituted 5–6 membered ring which may contain further hetero atom together with nitrogen atom bonded themselves.
R$^{11C}$ is hydrogen atom, C1–C6 alkyl, substituted or unsubstituted C2–C7 acyl, or tri(C1–C6)hydrocarbon-silyl or a group capable to form acetal with oxygen atom of hydroxy;
R$^{1C}$ and R$^{2C}$, same or different, are hydrogen atom, halogen atom, methyl or ethyl, $R^{3C}$ is hydrogen atom or a bond together with $R^{1C}$;

$R^{4C}$ and $R^{5C}$, same or different, are hydrogen atom, tri(C1–C6)hydrocarbon-silyl or a group capable to form acetal with oxygen atom of hydroxy.

$R^{6C}$ is hydrogen atom, methyl or ethynyl optionally protected;

$R^{7C}$ is C3–C8 alkyl or substituted or unsubstituted 5–6 membered alicyclic ring.

nc is 0 or 1).

In the prior arts described compounds of the formula (A) and (B), these compounds wherein the 7th carbon atom are replaced by a sulfur atom are hard to be metabolized and are useful for anti-aggregation. In the prior art concerning compounds of the formula (C), these compounds are useful for controlling vascular action.

DISCLOSURE OF THE INVENTION

The present invention provides (1) a 3,7-dithiaprostanoic acid derivative of the formula (I):

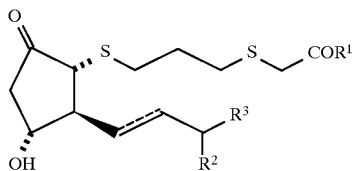

(wherein $R^1$ is hydroxy, C1–4 alkoxy or a group of the formula:

—$NR^6R^7$ wherein $R^6$ and $R^7$, independently, are hydrogen atom or C1–4 alkyl, $R^2$ is hydrogen atom or hydroxy, $R^3$ is (i) C1–8 alkyl, C2–8 alkenyl or C2–8 alkynyl,
(ii) phenyl or C3–7 cycloalkyl,
(iii) C1–8 alkyl, C2–8 alkenyl or C2–8 alkynyl substituted by phenyl or C3–7 cycloalkyl, with the proviso that, alkyl, alkenyl, alkynyl in (i) or (iii) may be substituted by one hydroxy group, when $R^2$ is hydrogen atom;

the symbol - - - is a double or single bond;

the formula including the 8-epi equilibrium compound thereof);

a non-toxic salt thereof or a cyclodextrin clathrate thereof, (2) processes for the preparation of them and (3) pharmaceutical agents containing them as active ingredient.

In the formula (I), C1–4 alkoxy represented by $R^1$ means methoxy, ethoxy, propoxy, butoxy groups and isomeric groups thereof.

In the formula (I), C1–4 alkyl represented by $R^6$ and $R^7$ means methyl, ethyl, propyl, butyl groups and isomeric groups thereof.

In the formula (I), C1–8 alkyl represented by $R^3$ and in $R^3$ means methyl, ethyl, propyl, butyl, pentyl, hexyl, heptyl, octyl groups and isomeric groups thereof.

In the formula (I), C2–8 alkenyl represented by $R^3$ and in $R^3$ means vinyl, propenyl, butenyl, pentenyl, hexenyl, heptenyl, octenyl groups and isomeric groups thereof.

In the formula (I), C2–8 alkynyl represented by $R^3$ and in $R^3$ means ethynyl, propynyl, butynyl, pentynyl, hexynyl, heptynyl, octynyl groups and isomeric groups thereof.

In the formula (I), C3–7 cycloalkyl represented by $R^3$ and in $R^3$ means cyclopropyl, cyclobutyl, cyclopentyl, cyclohexyl, cycloheptyl.

In this specification the symbol:

indicates a double or single bond, unless otherwise specified, the tapered line:

indicates that the substituent attached thereto is in front of the sheet, the symbol:

indicates that the substituent attached thereto is behind the sheet, the symbol:

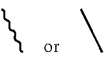

indicates that the substituent attached thereto is a mixture of in front of and behind the sheet or may be in front of or behind the sheet.

Unless otherwise specified, all isomers are included in the invention. For example, alkyl, alkylene and alkenylene includes straight-chain and branched-chain. Double bond in alkenylene includes E, Z and EZ mixtures. Isomers generated by the existence of asymmetric carbon(s) e.g. in branched alkyl are included in the present invention.

Among the compounds of the present invention, preferred configuration of compounds wherein $R^2$ is hydroxy in α-configuration i.e. natural configuration.

The configuration of 8th position of the compounds of the present invention are shown as α, but as is known in the art, these 8α-compounds are an equilibrium state with 8β-compounds (8-epi compound). Therefore the compounds of the formula (I) mean mixture of 8α-compound and isomeric 8β-compound.

Among the compounds of the present invention of the formula (I), preferred compounds are compounds shown in examples, the following compounds and corresponding esters and amides.

TABLE 1

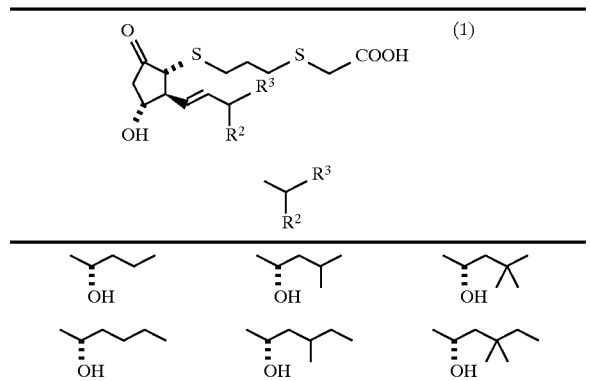

TABLE 1-continued
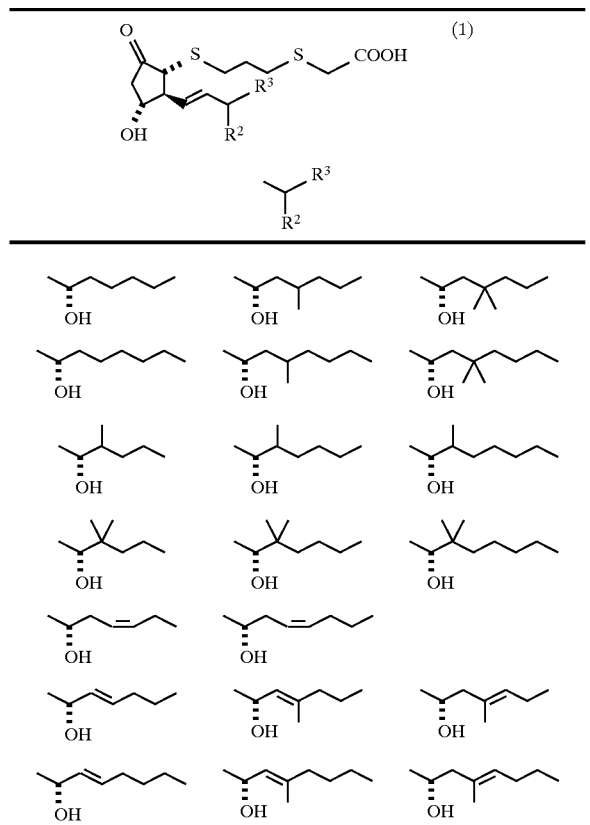
TABLE 2
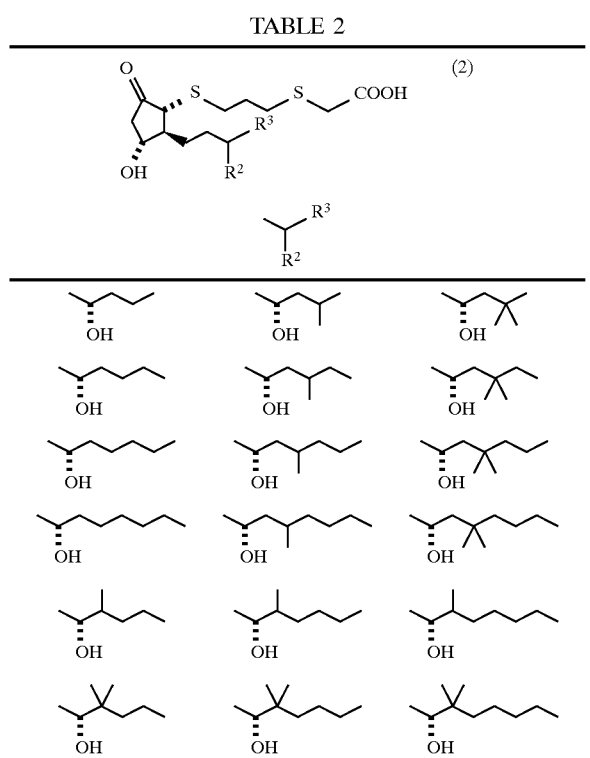
TABLE 2-continued
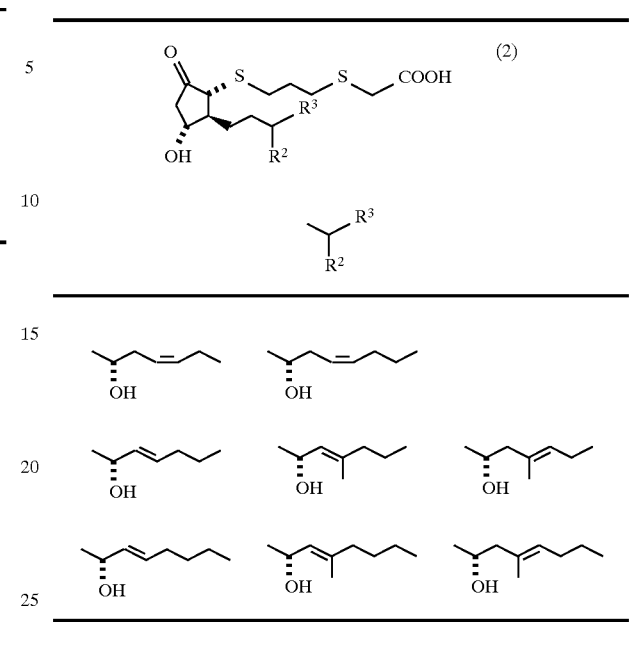
TABLE 3
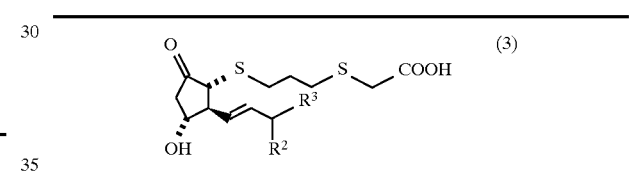
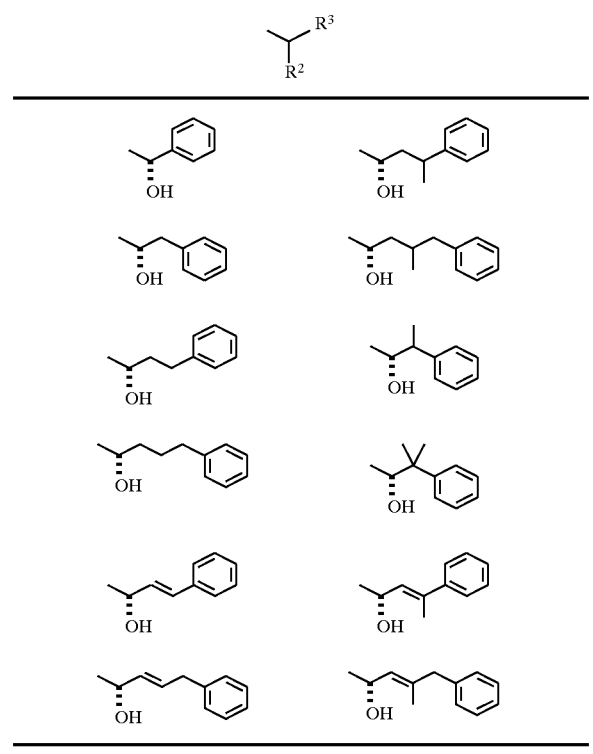

TABLE 4
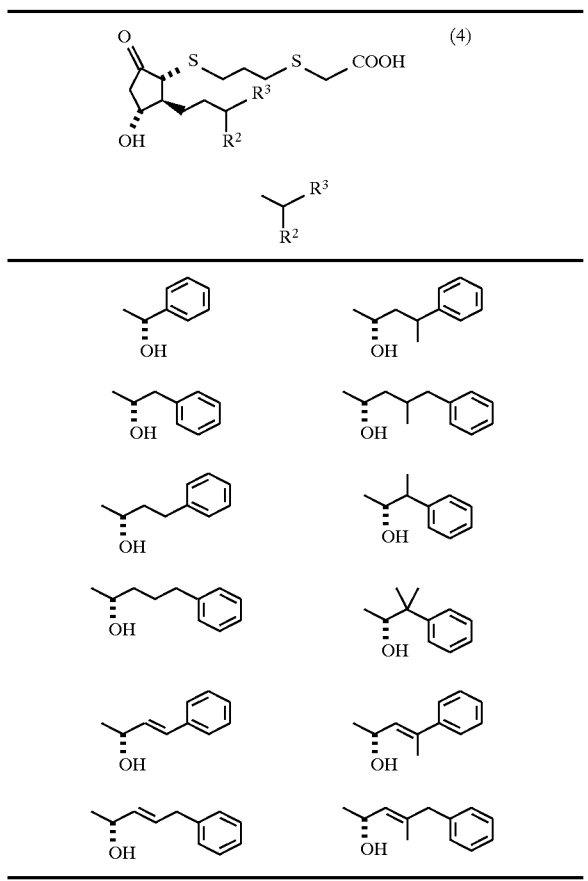
TABLE 5
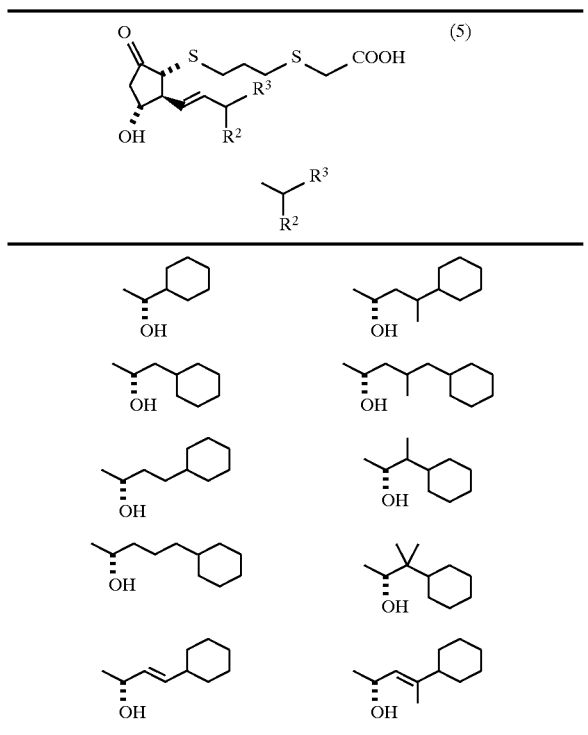
TABLE 5-continued
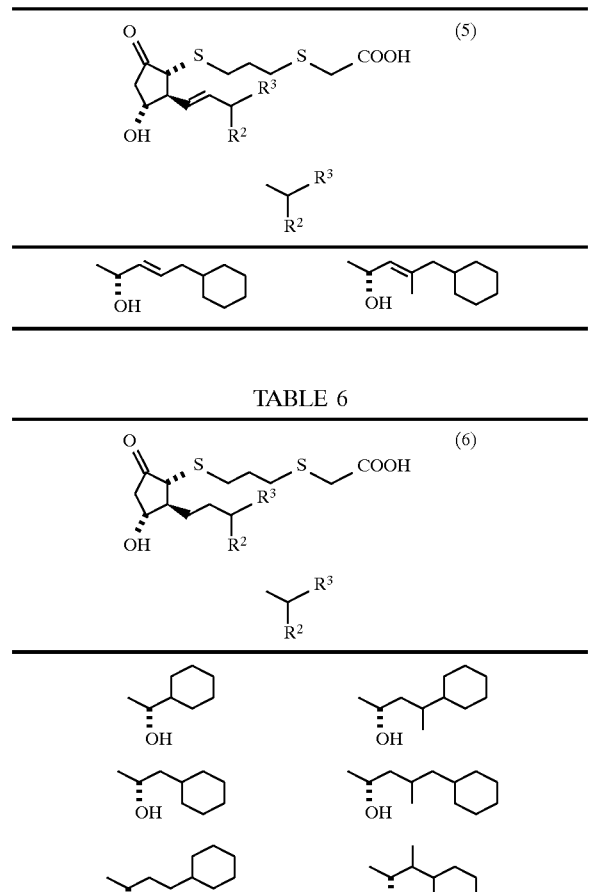
TABLE 6
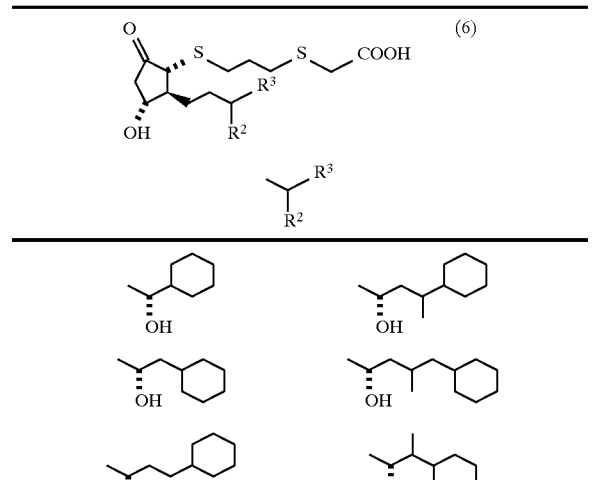
TABLE 7
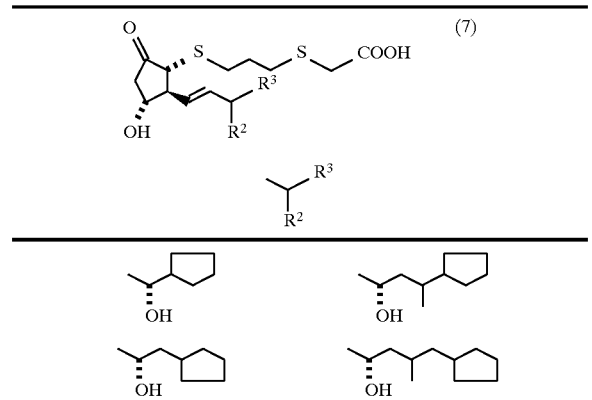

TABLE 7-continued
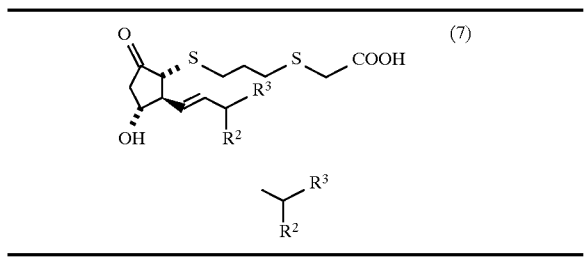
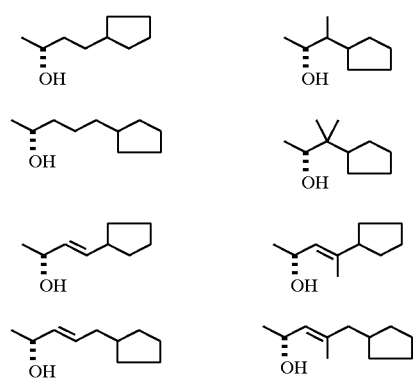
TABLE 8
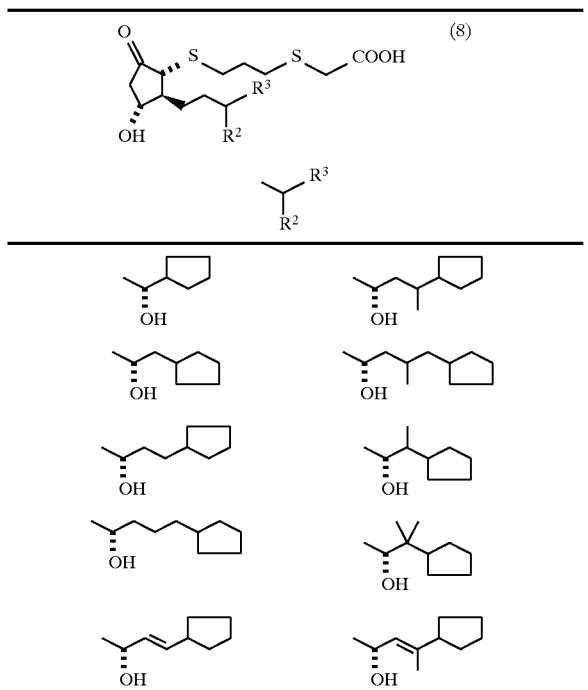
TABLE 8-continued
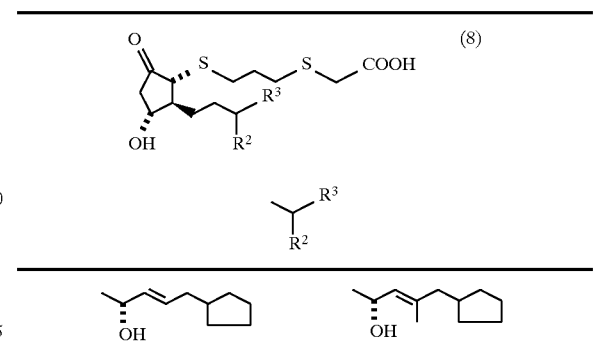
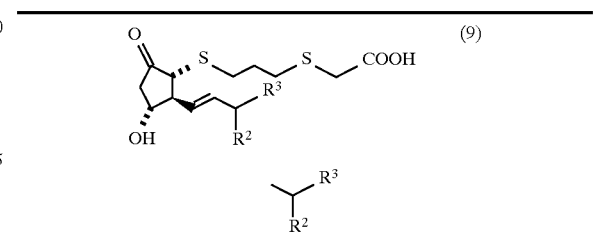
TABLE 9
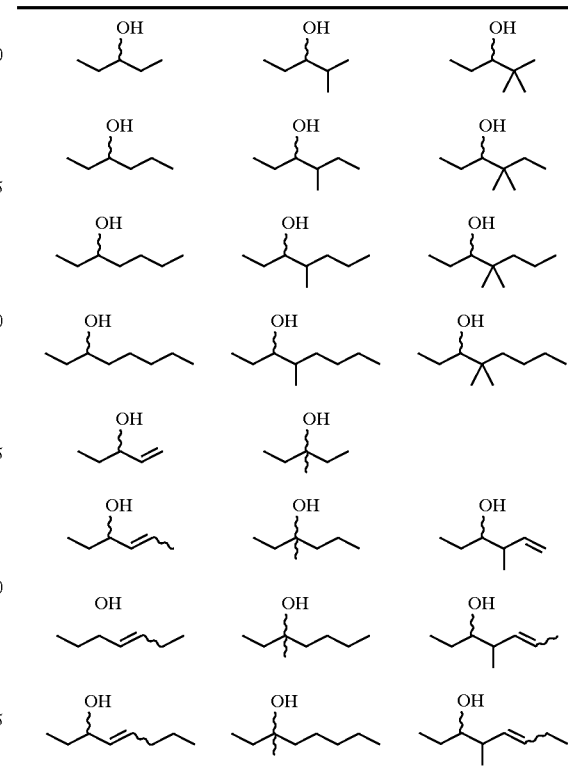

TABLE 10
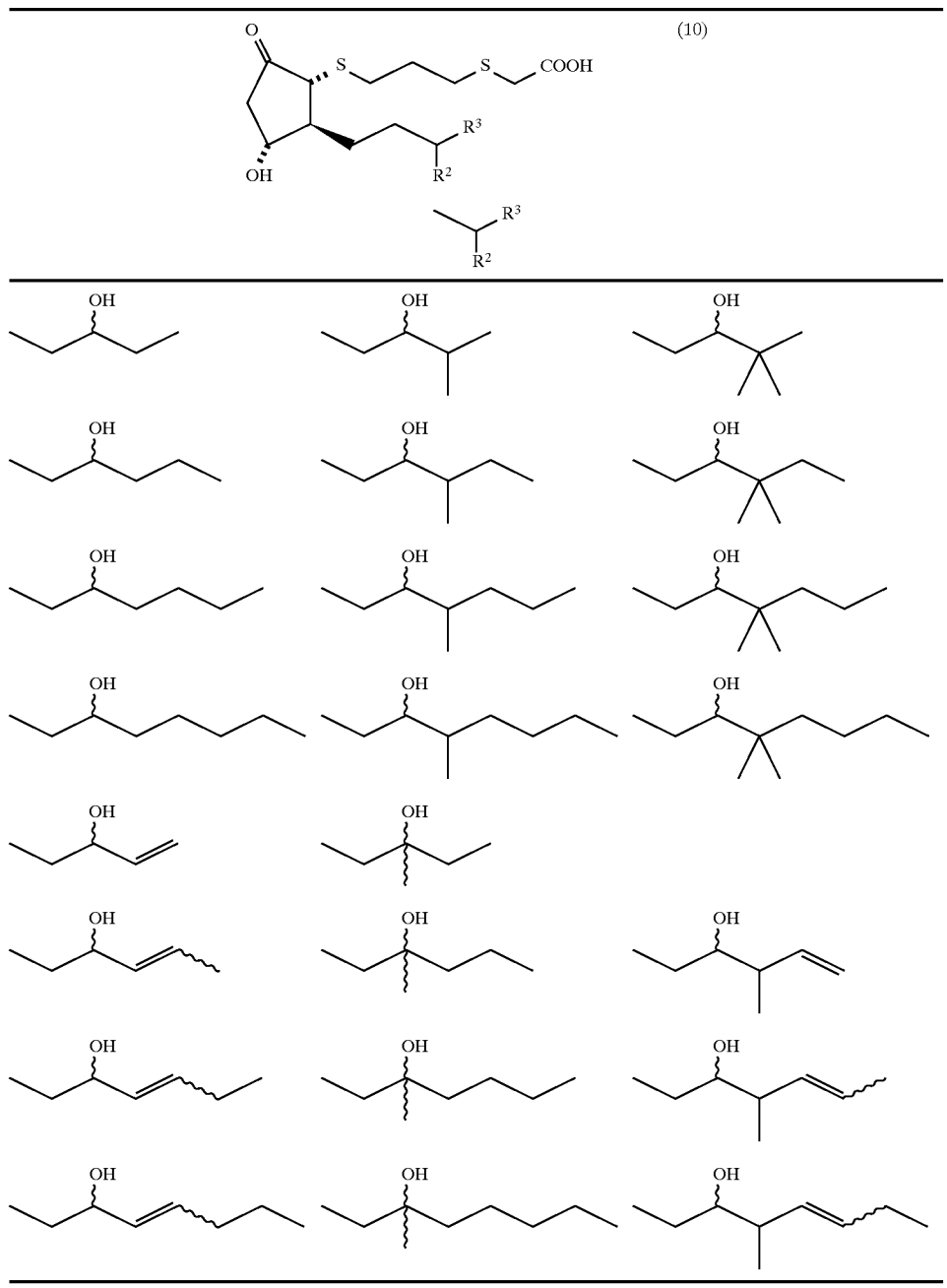

TABLE 11
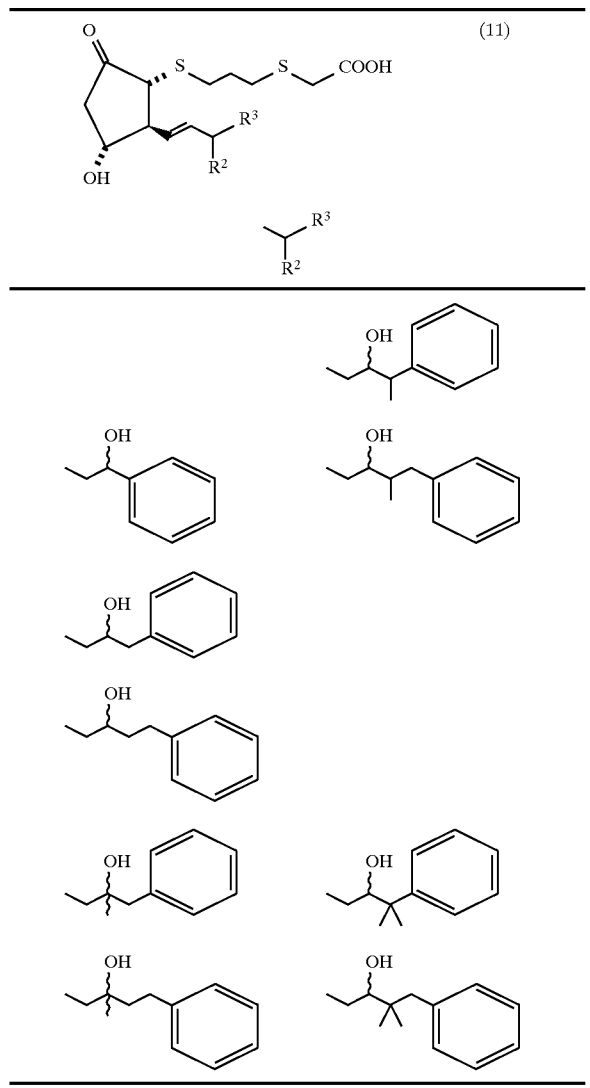
TABLE 12
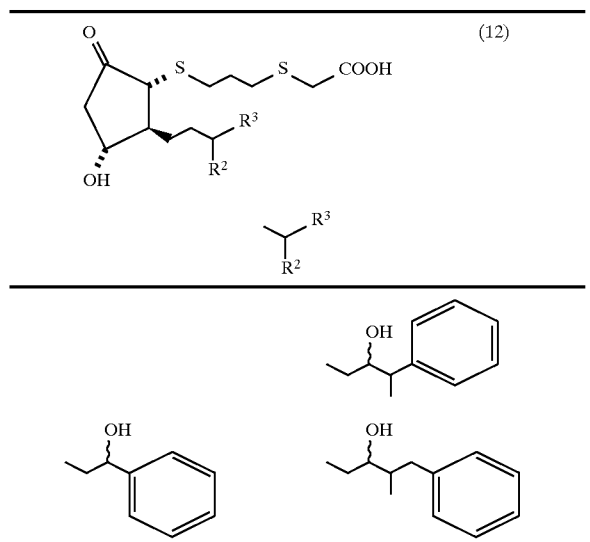
TABLE 12-continued
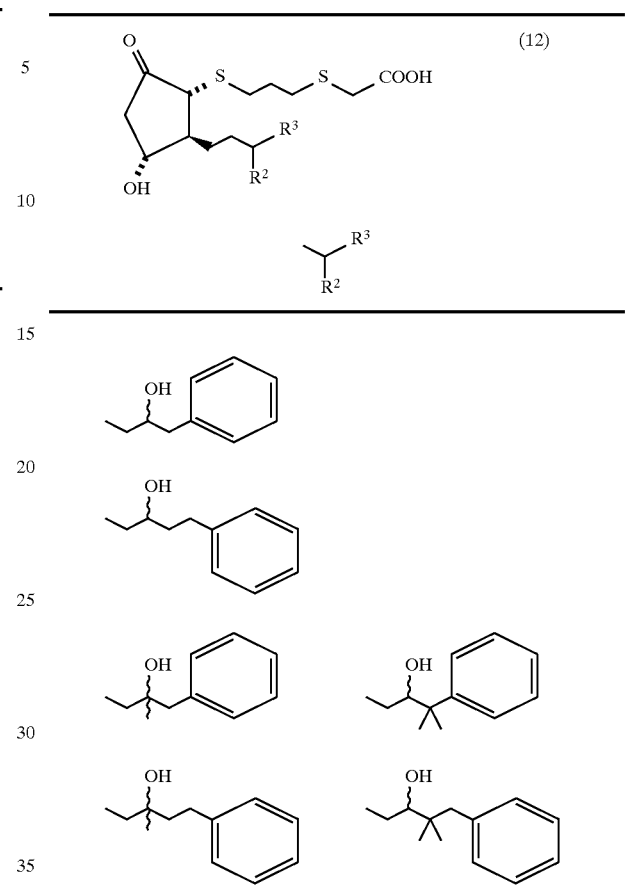
TABLE 13
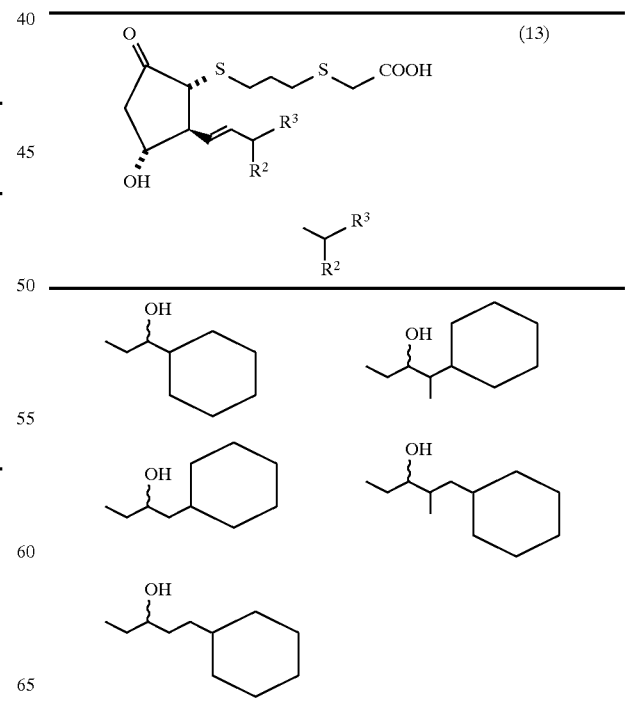

TABLE 13-continued (13)

TABLE 14

(14)

TABLE 15

(15)

TABLE 16

(16)

TABLE 16-continued

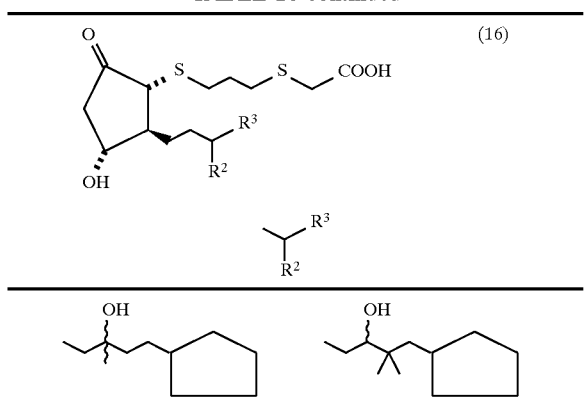

Salts

The compounds of the formula (I) may be converted into the corresponding salts. Non-toxic and water-soluble salts are preferable. Suitable salts, for example, are as follows:
  salts of alkali metal (sodium, potassium etc.), salts of alkaline earth metal (calcium, magnesium etc.), ammonium salts, salts of pharmaceutically acceptable organic amine (tetramethylammonium, triethylamine, methylamine, dimethylamine, cyclopentylamine, benzylamine, phenethylamine, piperidine, monoethanolamine, diethanolamine, tris (hydroxymethyl)aminomethane, lysine, arginine, N-methyl-D-glucamine etc.).

Cyclodextrin clathrates

Cyclodextrin clathrates of 3,7-dithiaprostanoic acid derivatives of the formula (I) may be prepared by the method described in GB 1351238 using α-, β- or γ-cyclodextrin or a mixture thereof. Converting into their cyclodextrin clathrates serves to increase the stability and solubility in water of the compounds, and therefore it is useful in the use for pharmaceuticals.

Processes for the Preparation (1) Among the compounds of the formula (I), compounds of formula (Ia):

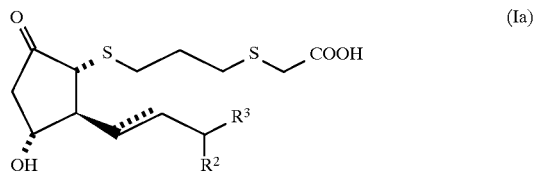

(wherein all symbols are the same meaning as hereinbefore defined) may be prepared by hydrolyzing a compound of formula (Ib):

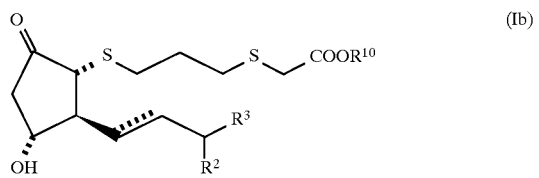

(wherein $R^{10}$ is C1–4 alkyl and the other symbols are the same meaning as hereinbefore defined) with an enzyme.

Hydrolysis with an enzyme is known, for example, it may be carried out in a mixture of a water-miscible organic solvent (ethanol, dimethylsulfoxide etc.) and water, in the presence or absence of buffer, using an ester cleaving enzyme (esterase, lipase etc.), at 0°–50° C.

(2) Among the compounds of the formula (I), compounds of formula (Ic):

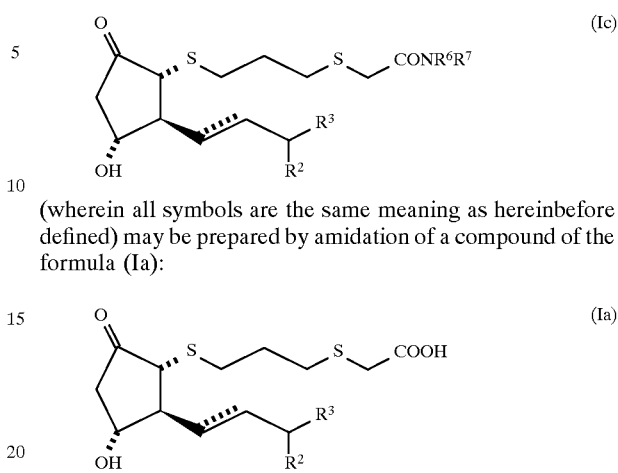

(wherein all symbols are the same meaning as hereinbefore defined) may be prepared by amidation of a compound of the formula (Ia):

(wherein all symbols are the same meaning as hereinbefore defined) with a compound of formula (III):

$$HNR^6R^7 \qquad (III)$$

(wherein all symbols are the same meaning as hereinbefore defined).

Amidation is known reaction, for example, in an inert organic solvent (tetrahydrofuran (THF), methylene chloride, benzene, acetone, acetonitrile or a mixture thereof etc.), in the presence or absence of tertiary amine (dimethylaminopyridine, pyridine, triethylamine etc.), using a condensing agent (1-ethyl-3-[3-(dimethylamino)propyl] carbodiimide (EDC), 1,3-dicyclohexylcarbodiimide (DCC) etc.), at 0°–50° C.

(3) Among the compounds of the formula (I), compounds of the formula (Ib):

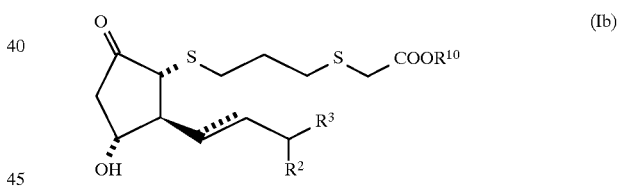

(wherein all symbols are the same meaning as hereinbefore defined) may be prepared by hydrolyzing a compound of formula (II):

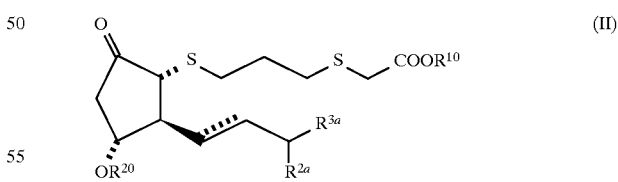

(wherein $R^{2a}$ is hydrogen atom or hydroxy protected by a protecting group which is eliminated under an acidic condition, $R^{20}$ is a protecting group which is eliminated under an acidic condition, $R^{3a}$ is (I) C1–8 alkyl, C2–8 alkenyl or C2–8 alkynyl, (ii) phenyl or C3–7 cycloalkyl, (iii) C1–8 alkyl, C2–8 alkenyl or C2–8 alkynyl which are substituted by phenyl or C3–7 cycloalkyl (with the proviso that when $R^{2a}$ is hydrogen, alkyl, alkenyl and alkynyl groups in (I) or (iii) may be substituted by hydroxy protected by a protecting group which is eliminated under an acidic condition;) the symbol:

is a double or single bond)
in an acidic condition.

A protecting group which is eliminated under an acidic condition means, for example, t-butyldimethylsilyl, triphenylsilyl, triphenylmethyl, tetrahydropyranyl, 1-ethoxyethyl, methoxymethyl, trimethylsilyl etc.

Hydrolysis under an acidic condition is known, for example, in a water-miscible organic solvent (THF, methanol, ethanol, dimethoxyethane, acetonitrile or a mixture thereof etc.), using inorganic acid (hydrochloric acid, phosphoric acid, hydrofluoric acid, hydrogen fluoride-pyridine complex etc.) or organic acid (acetic acid, toluene-sulphonic acid, trichloroacetic acid etc.), at 0°–50° C.

The compound of the formula (II) may be prepared by the following reaction scheme (A) in the next sheet.

Symbols in reaction scheme are the same meaning as hereinbefore defined.

Starting Materials and Reagents

Starting materials and reagents are known per se or may be prepared by known methods.

Properties of the Compound of the Invention

The compounds of the present invention of the formula (I) bind and act on EP4 receptor which is a subtype of $PGE_2$ receptor.

In a standard laboratory test, the activities of the compounds of the present invention were confirmed by binding assay using expression cell of the prostanoid receptor subtype.

(I) Binding assay using expression cell of the prostanoid receptor subtype

The preparation of membrane fraction was carried out according to the method of Sugimoto et al (J. Biol. Chem. 267, 6463–6466 (1992)) using the prostanoid receptor subtypes (mouse EP3α, EP4) expressing CHO cells.

The standard assay mixture containing membrane fraction (0.5 mg/ml) and $^3H$-$PGE_2$ in a final volume of 200 μl was incubated for 1 hour at room temperature. The reaction was terminated by the addition of 3 ml of ice-cold buffer. The mixture was rapidly filtered through a GF/B glass filter. The

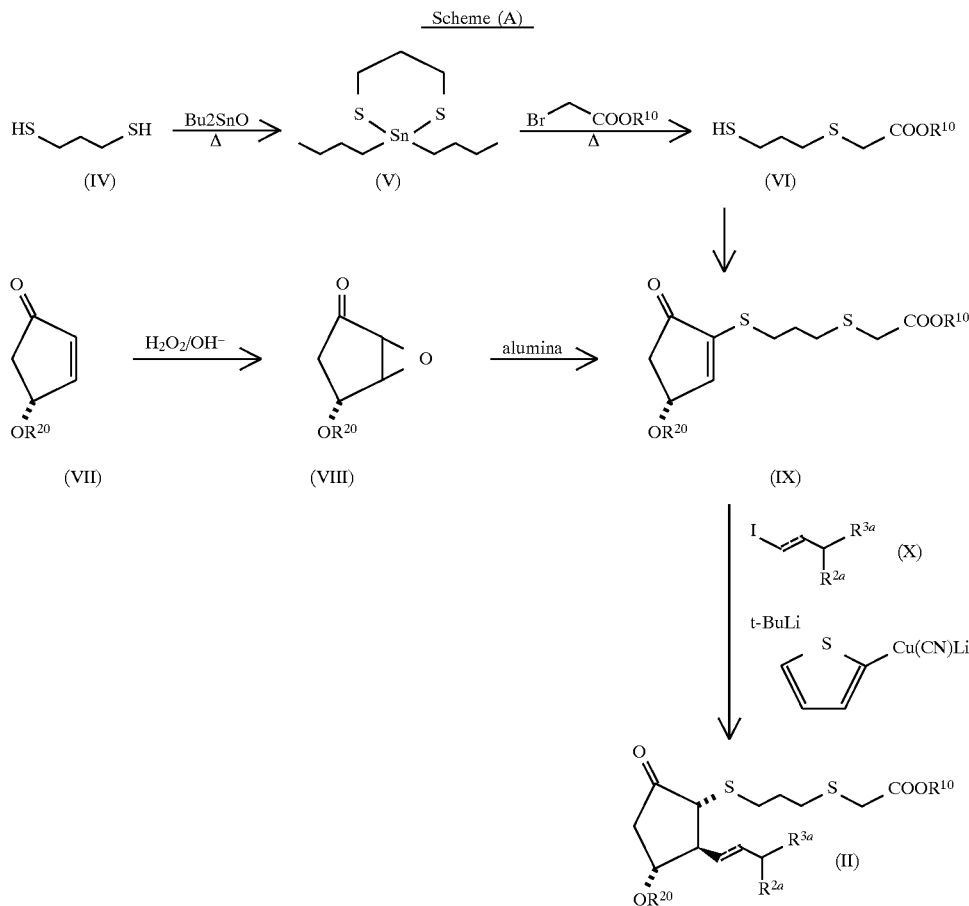

Scheme (A)

In each reaction in this specification products may be purified by conventional manner. For example, it may be carried out by distillation under atmospheric or reduced pressure, high performance liquid chromatography, thin layer chromatography or column chromatography using silica gel or magnesium silicate, washing or recrystallization. Purification may be carried out after each reaction, or after a series of reactions.

radioactivity associated with the filter was measured by liquid scintillation counting.

Kd and Bmax value were determined from Scatchard plots (Ann. N. Y. Sci., 51, 660 (1949)). Non-specific binding was calculated as the bound in the presence of an excess (2.5 μM) of unlabeled $PGE_2$.

In the experiment for competition of specific $^3H$-$PGE_2$ binding by the compounds of the present invention, 2.5 nM of $^3$H-PGE$_2$ and various concentration of the compounds of the present invention were added. The following buffer was used in all reactions. Buffer: 10 mM potassium phosphate (pH 6.0), 1 mM EDTA, 10 mM MgCl$_2$, 0.1M NaCl. The dissociation constant (Ki) of each compound was calculated by the following equation.

$$Ki=IC_{50}/(1+[C]/Kd))$$

Results are shown in Table 17 and 18.

TABLE 17

| Example No. | Dissociation constant for EP4 Ki($\mu$M) |
| --- | --- |
| 2 | 0.0007 |
| 2(a) | 0.0008 |
| 2(b) | 0.0006 |
| 2(c) | 0.0056 |
| 2(d) | 0.0016 |
| 2(e) | 0.00091 |
| 2(f) | 0.007 |
| 2(g) | 0.006 |
| 2(h) | 0.022 |
| 2(k) | 0.0007 |
| 2(m) | 0.0014 |
| 2(o) | 0.0002 |
| 2(q) | 0.0004 |
| 2(t) | 0.0042 |

TABLE 18

| Example No. | Dissociation constant for EP3$\alpha$ Ki($\mu$M) |
| --- | --- |
| 2 | 1.5 |
| 2(a) | 0.01 |
| 2(f) | 0.13 |
| 2(h) | 0.61 |
| 2(k) | 0.034 |
| 2(m) | 0.023 |
| 2(o) | 0.025 |

Toxicity

On the other hand, toxicity of the compounds of the present invention of the formula (I) are very low, and are therefore, it may be estimated to be safe for pharmaceutical use.

Application for Pharmaceuticals

The compounds of the present invention of the formula (I) bind strongly and act on PGE$_2$ receptor, especially on EP4 subtype receptor and therefore are useful for prevention and/or treatment of immunologic diseases (autoimmune diseases, organ transplantation etc.), asthma, abnormal bone formation, neuronal cell death, liver damage, nephritis, hypertension, myocardiac ischemia etc.

Among the compounds of the present invention of the formula (I), compounds which bind weakly to receptor subtypes except for EP4 receptors do not express other effects and therefore it is thought that such compounds will be a medical agent which have less side-effects.

For the purpose described above, the compounds of the present invention of the formula (I), non-toxic salts thereof or cyclodextrin clathrates thereof may be normally administered systemically or locally, usually by oral or parenteral administration.

The doses to be administered are determined depending upon age, body weight, symptom, the desired therapeutic effect, the route of administration, and the duration of the treatment etc. In the human adult, the doses per person per dose are generally between 1 $\mu$g and 100 mg, by oral administration, up to several times per day, and between 0.1 $\mu$g and 10 mg, by parenteral administration up to several times per day, or continuous administration between 1 and 24 hrs. per day from vein.

As mentioned above, the doses to be used depend upon various conditions. Therefore, there are cases in which doses lower than or greater than the ranges specified above may be used.

When administration of the compounds of the present invention, it is used as solid compositions, liquid compositions or other compositions for oral administration, as injections, liniments or suppositories etc. for parenteral administration.

Solid compositions for oral includes tablets, pills, capsules, dispersible powders, granules. Capsules include soft capsules and hard capsules.

In such compositions, one or more of the active compound(s) is or are, admixed with at least one inert diluent such as lactose, mannitol, glucose, hydroxypropylcellulose, microcrystalline cellulose, starch, polyvinylpyrrolidone or magnesium metasilicate aluminate.

The compositions may also comprise, as is normal practice, additional substances other than inert diluents e.g. lubricating agents such as magnesium stearate, disintegrating agents such as cellulose calcium glycolate, stabilizing agents e.g. lactose and agents to assist dissolution e.g. arginine, glutamic acid or aspartic acid. The tablets or pills may, if desired, be made into gastric film-coated tablets or pills, such as sugar-coated, gelatin-coated, hydroxypropyl cellulose-coated hydroxypropylmethyl cellulose phthalate-coated tablets or pills; two or more layers may be used. The compositions for oral administration also include capsules of absorbable material such as gelatin.

Liquid compositions for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavoring, perfuming and preserving agents.

Other compositions for oral administration include spray compositions which may be prepared by known methods and which comprise one or more of the active compound(s). Spray compositions may comprise additional substances other than inert diluents: e.g. stabilizing agents (sodium sulfate etc.), isotonic buffer (sodium chloride, sodium citrate, citric acid etc.). For preparation of such spray compositions, for example, the method described in the U.S. Pat. No. 2,868,691 or U.S. Pat. No. 3,095,355 may be used.

Injections for parenteral administration include sterile aqueous or non-aqueous solutions, suspensions and emulsions. Aqueous solutions, suspensions include distilled water for injection and physiological salt solution. Non-aqueous solutions, suspensions include propylene glycol, polyethylene glycol, vegetable oil such as olive oil, alcohol such as ethanol, POLYSORBETE 80 (registered trade mark), etc.

Such compositions may comprise additives other than inert diluents: e.g. preserving agents, wetting agents, emulsifying agents, dispersing agents, stabilizing agents, assisting agents such as assisting agents for dissolving (glutamic acid, asparginic acid etc.). They may be sterilized, for example, by filtration through a bacteria-retaining filter, by incorporation of sterilizing agents in the compositions or by irradiation. They may also be manufactured in the form of sterile solid compositions and which may be dissolved in sterile water or some other sterile diluent(s) for injection immediately before used.

Other compositions for parenteral administration include liquids for external use, and endermic liniments, ointment, suppositories for rectal administration and pessaries for vaginal administration which comprise one or more of the active compound(s) and may be prepared by per se known methods.

REFERENCE EXAMPLES AND EXAMPLES

The following reference examples and examples illustrate the present invention, but not limit the present invention.

The solvents in parentheses show the developing or eluting solvents and the ratios of the solvents used are by volume in chromatographic separations. Unless otherwise specified "NMR" were measured in a solution of CDCl$_3$.

Reference Example 1

2,2-dibutyl-2-stanane-1,3-dithiane

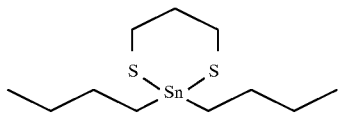

A solution of 1,3-propanedithiol (3.0 g) and dibutyl stanane oxide (6.9 g) in benzene was refluxed. The reaction mixture was evaporated to give the title compound having the following physical data.

TLC: Rf 0.68 (hexane:EtOAc=9:1).

Reference Example 2

6-Mercapto-3-thiahexanoic acid methyl ester

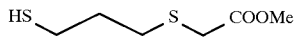

Bromoacetic acid methyl ester (6.36 g) was added to a solution of 2,2-dibutyl-2-stanane-1,3-dithiane (9.38 g) in anhydrous dimethylformamide (DMF, 20 ml). The mixture was stirred for 3 hrs at 100° C. After cooling, water was added to the reaction mixture. The mixture was stirred for 1 hr. The reaction mixture was extracted with ethyl acetate. The organic layer was washed, dried and evaporated. The residue was purified by column chromatography on silica gel (hexane-ethyl acetate) to give the title compound (2.61 g) having the following physical data.

TLC: Rf 0.60 (hexane:EtOAc=4:1).

Reference Example 3

7-(4R-t-butyldimethylsilyloxycyclopentenon-2-yl)-3,7-dithiaheptanoic acid methyl ester

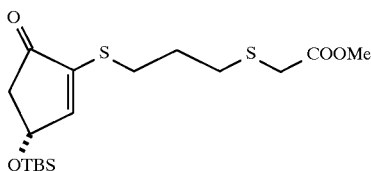

4R-t-butyldimethylsilyloxy-2-cyclopentenone (2.76 g) in methanol (40 ml) was cooled with ice. An aq. solution of hydroperoxide (31%, 5 ml) and a 1N aq. solution of sodium hydroxide (0.05 ml) were added to the solution. The mixture was stirred for 1.5 hrs at the same temperature. Saturated aq. solution of ammonium chloride was added to the reaction mixture and the mixture was extracted. The organic layer was washed, dried and evaporated. The residue was dissolved in chloroform (35 ml). A solution of 6-mercapto-3-thiahexanoic acid methyl ester (2.34 g) in chloroform (10 ml) and active alumina (13 g) were added to the solution. The mixture was stirred overnight at room temperature. The reaction mixture was filtered. The filtrate was evaporated and purified by column chromatography on silica gel (hexane-ethyl acetate) to give the title compound (3.21 g) having the following physical data.

TLC: Rf 0.39 (hexane:EtOAc=4:1).

Reference Example 4

11α,15α-bis(t-butyldimethylsilyloxy)-9-oxo-3,7-dithiaprost-13-enoic acid methyl ester

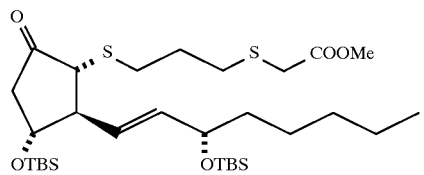

Under an atmosphere of argon, 1.57M solution of t-butyl lithium in pentane (1.01 ml) was dropped to a solution of (3S)-1-iodo-3-t-butyldimethylsilyloxy-1-octene (290 mg) in anhydrous ether (4 ml). The mixture was stirred for 1 hr at the same temperature. A 0.25M solution of lithium copper 2-thienylcyanide in THF (3.38 ml) was dropped to the solution at −78° C. The reaction mixture was stirred for 30 mins at the same temperature. A solution of 7-(4R-t-butyldimethyl-silyloxycyclopentenon-2-yl)-3,7-dithiaheptanoic acid methyl ester (220 mg; prepared in Reference Example 3) in anhydrous THF (4 ml) was dropped to the solution at −78° C. The reaction mixture was stirred for 1 hr. An aq. saturated solution of ammonium chloride was added to the mixture. The mixture was warmed to room temperature. The reaction mixture was extracted by hexane. The organic layer was washed, dried, evaporated and purified by column chromatography on silica gel (hexane-ethyl acetate) to give the title compound (258 mg) having the following physical data.

TLC: Rf 0.55 (hexane:EtOAc=4:1).

Example 1

11α,15α-dihydroxy-9-oxo-3,7-dithiaprost-13E-enoic acid methyl ester

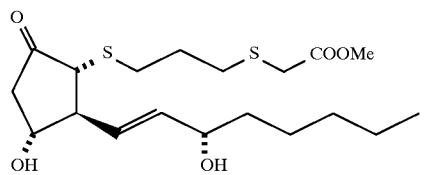

Pyridine (1.2 ml) and hydrogen fluoride-pyridine (2 ml) were added to a solution of 11α,15α-bis(t-butyldimethylsilyloxy)-9-oxo-3,7-dithiaprost-13E-enoic acid methyl ester (220 mg; prepared in Reference Example 4) in acetonitrile (8 ml) cooled with ice. The reaction mixture was stirred for 1 hr at room temperature. The reaction mixture was poured into a mixture of ethyl acetate and an aq. saturated sodium bicarbonate cooled at 0° C. The mixture was extracted with ethyl acetate. The organic layer was washed, dried and evaporated. The residue was purified by column chromatography on silica gel (chloroform-methanol) to give the title compound (123 mg; equilium mixture with 8-epi compound) having the following physical data.

TLC: Rf 0.55 (CHCl3:CH3OH=19:1);

NMR: δ5.73 (1H, dd), 5.63 (1H, dd), 4.44 and 4.13 (2H, each m), 3.74 (3H, s), 3.23 (2H, s), 3.40–2.18 (8H, m), 1.98–1.20 (10H, m), 0.90 (3H, t).

Example 2

11α,15α-dihydroxy-9-oxo-3,7-dithiaprost-13E-enoic acid

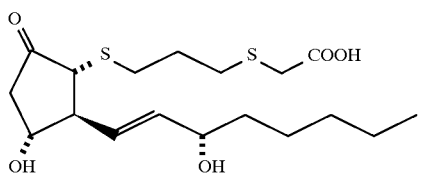

Phosphate buffer (10 ml; pH 7.4) was added to a solution of 11α,15α-dihydroxy-9-oxo-3,7-dithiaprost-13E-enoic acid methyl ester (48 mg; prepared in Example 1) in ethanol (1 ml). Pig liver esterase was added to the reaction mixture. The mixture was stirred for 2 hrs at room temperature. A saturated aq. solution of ammonium sulfate was added to the mixture. The mixture was extracted by ethyl acetate. The organic layer was dried, evaporated. The residue was purified by column chromatography on silica gel (ethyl acetate) to give the title compound (39 mg; a equiblium mixture with 8-epi isomer) having the following physical data.

TLC: Rf 0.10 (EtOAc);

NMR: δ5.79 (1H, dd), 5.64 (1H, dd), 4.3–4.1 (2H, m), 3.7 (1H, bs), 3.23 (2H, s), 3.0–2.4 (8H, m), 2.0–1.8 (2H, m), 1.7–1.5 (2H, m), 1.4–1.2 (6H, m), 1.0–0.8 (3H, m).

Example 2(a)–2(u)

Compounds having the following physical data were given by the same manner in Reference Example 4, Example 1 and 2. These compounds are equibulium mixtures with 8-epi isomers.

Example 2(a)

11α,15α-dihydroxy-9-oxo-17β,20-dimethyl-3,7-dithiaprost-13E-enoic acid

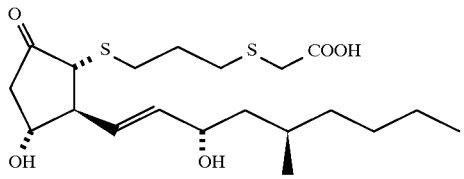

TLC: Rf 0.50, 0.44 (CHCl3:CH3OH=9:1, 1% acetic acid);

NMR: δ5.75(2H, m), 5.06(3H, br), 4.53–4.05(2H, m), 3.42–2.18(8H, m), 3.23(2H, s), 1.88(2H, m), 1.58(2H, m), 1.42–1.03(7H, m), 0.91(6H, m).

Example 2(b)

11α,15α-dihydroxy-9-oxo-17α,20-dimethyl-3,7-dithiaprost-13E-enoic acid

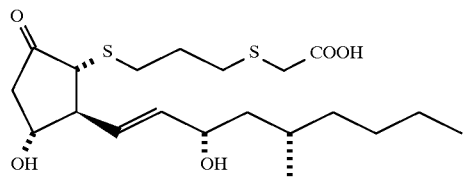

TLC: Rf 0.38, 0.22 (EtOAc:AcOH=100:1);

NMR: δ5.74 (1H, dd), 5.67 (1H, dd), 4.77 (3H, br), 4.45 and 4.20(2H, each m), 3.23 (2H, s), 3.42–2.18 (8H, m), 1.88 (2H, m), 1.62–1.04 (9H, m), 0.89 (6H, m).

Example 2(c)

11α,16β-dihydroxy-9-oxo-16α-methyl-3,7-dithiaprost-13E-enoic acid

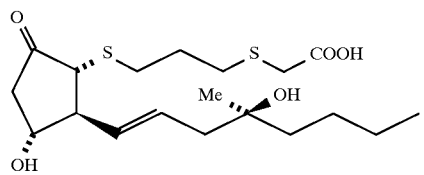

TLC: Rf 0.30, 0.23 (EtOAc:hexane:AcOH=6:2:1);

NMR: δ5.9–5.7 (1H, m), 5.7–5.5 (1H, m), 4.5 and 4.1(1H, each m), 4.1–3.7 (3, br), 3.55–3.45 and 3.2–2.2 (10H, each m), 3.24 (2H, s), 2.0–1.8 (2H, m), 1.6–1.1 (6H, m), 1.23 (3H, s), 0.93 (3H, t).

Example 2(d)

11α,15α-dihydroxy-9-oxo-3,7-dithiaprostanoic acid

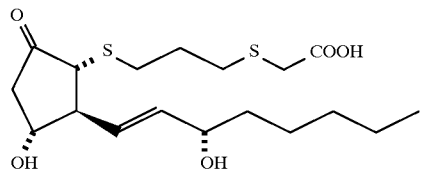

TLC: Rf 0.30 (EtOAc:AcOH=100:1);

NMR: δ5.25 (3H, br), 4.32 and 4.15(1H, each m), 3.72 (1H, m), 3.23 (2H, s), 3.38–2.38 (7H, m), 2.24 (1H, m), 2.08–1.12 (14H, m), 0.90 (3H, t).

Example 2(e)

11α,15α-dihydroxy-9-oxo-3,7-dithiaprost-13E,17Z-dienoic acid

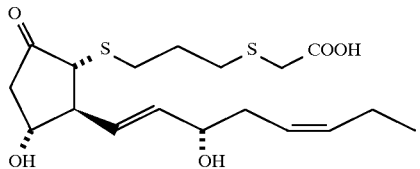

TLC: Rf 0.52, 0.41 (EtOAc:AcOH=20:1);

NMR: δ5.9–5.5 (3H, m), 5.5–5.2 (1H, m), 4.6–4.2 (5H, br), 3.24 (2H, s), 3.45–3.40 and 3.1–2.2 (8H, each m), 2.2–2.0 (2H, m), 2.0–1.8 (2H, m), 0.97 (3H, t).

Example 2(f)

11α,15α-dihydroxy-9-oxo-16-phenyl-17,18,19,20-tetranor-3,7-dithiaprost-13E-enoic acid

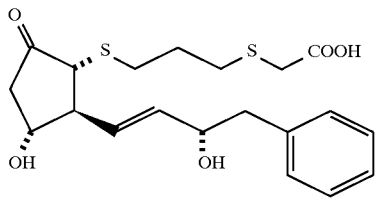

TLC: Rf 0.24 (EtOAc:CH3OH=2:1);

NMR: δ7.38–7.16 (5H, m), 5.90–5.50 (2H, m), 4.56–3.70 (7H, m), 3.21 (2H, s), 3.10–2.26 (10H, m), 1.87 (2H, quin).

Example 2(g)

11α,15α-dihydroxy-9-oxo-17-phenyl-18,19,20-trinor-3,7-dithiaprost-13E-enoic acid

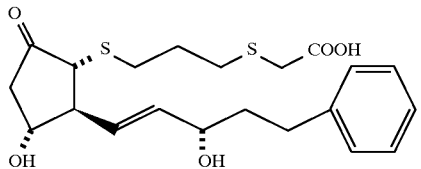

TLC: Rf 0.52, 0.43 (EtOAc:AcOH=20:1);

NMR: δ7.35–7.15 (5H, m), 5.9–5.6 (2H, m), 4.5–4.4 and 4.3–4.0 (2H, each m), 4.3–3.6 (3H, br), 3.03 (2H, s), 3.45–3.40 and 3.05–2.20 (10H, each m), 2.0–1.8 (4H, m).

Example 2(h)

11α,15α-dihydroxy-9-oxo-15-cyclohexyl-3,7-dithia-16,17,18,19,20-pentanorprost-13E-enoic acid

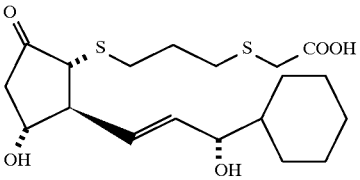

TLC: Rf 0.46, 0.40 (CHCl3:CH3OH=9:1, 1% ACOH);

NMR: δ5.77 (1H, m), 5.61 (1H, dd), 4.76 (3H, br), 4.45 and 4.14 (1H, each m), 3.92 (1H, m), 3.42–2.30 (8H, m), 3.23 (2H, s), 1.98–1.56 (7H, m), 1.54–0.85 (6H, m).

Example 2(i)

11α,15α-dihydroxy-9-oxo-15-cyclopentyl-3,7-dithia-16,17,18,19,20-pentanorprost-13E-enoic acid

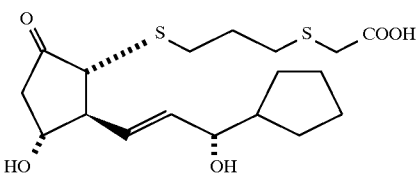

TLC: Rf 0.27 (CHCl3/MeOH, 4/1);

NMR: δ5.86–5.48 (2H, m), 4.70–3.20 (6H, m), 3.15 (2H, s), 3.08–1.00 (18H, m).

Example 2(j)

11α,15α-dihydroxy-9-oxo-16-cyclohexyl-3,7-dithia-17,18,19,20-tetranorprost-13E-enoic acid

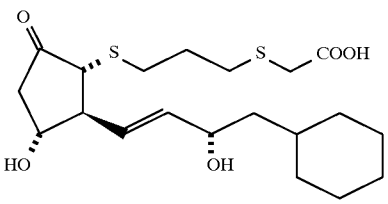

TLC Rf: 0.22 (AcOEt/AcOH, 50/1);

NMR: δ5.90–5.52 (2H, m), 5.04–4.40 (3H, br), 4.40–3.92 (3H, m), 3.22 (2H, s), 3.12–2.24 (7H, m), 2.24–0.70 (15H, m).

Example 2(k)

11α,15α-dihydroxy-9-oxo-15β-methyl-3,7-dithiaprost-13E-enoic acid

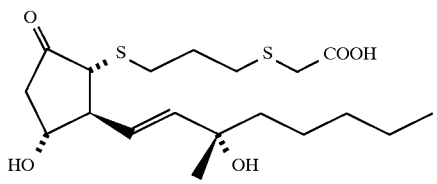

TLC: Rf 0.27 (AcOEt/AcOH, 50/1);

NMR: δ5.84–5.46 (2H, m), 5.36–4.70 (3H, br), 4.47–3.98 (2H, m), 3.15 (2H, s), 3.06–2.20 (7H, m), 2.04–1.72 (2H, m), 1.60–1.40 (2H, m), 1.32–1.10 (9H, m), 0.81 (3H, t, J=6.4 Hz).

Example 2(l)

11α,15α-dihydroxy-9-oxo-17-ethyl-3,7-dithia-20-norprost-13E-enoic acid

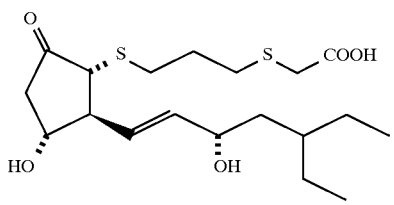

TLC: Rf 0.49, 0.38 (EtOAc/AcOH, 20:1);

NMR: δ5.9–5.6 (2H, m), 5.6–5.0 (3H, br), 4.6–4.0 (2H, m), 3.23 (2H, s) 3.45–3.40 and 3.1–2.2 (8H, m), 2.0–1.8 (2H, m), 1.6–1.2 (7H, m), 0.83 (6H, t, J=7 Hz).

Example 2(m)

11α,15α-dihydroxy-9-oxo-3,7-dithia-20-norprost-13E-enoic acid

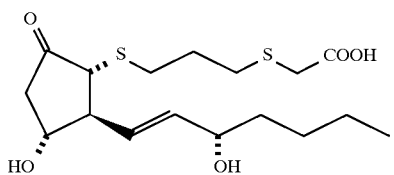

TLC: Rf 0.47, 0.37 (EtOAc/AcOH, 20:1);

NMR: δ5.85–5.60 (2H, m), 5.6–5.2 (3H, br), 4.5–4.4 and 4.25–4.05 (2H, m), 3.23 (2H, s), 3.45–3.40 and 3.1–2.2 (8H, m), 2.0–1.8 (2H, m), 1.7–1.2 (6H, m), 0.92 (3H, t, J=7 Hz).

Example 2(n)

11α,15α-dihydroxy-9-oxo-3,7-dithia-20-homoprost-13E-enoic acid

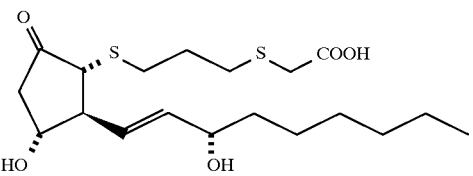

TLC: Rf 0.58, 0.46 (EtOAc/AcOH, 10/1);

NMR: δ5.71 (2H, m), 5.38 (3H, br), 4.45 and 4.17 (2H, each m), 3.42 and 3.03 (1H, each d, J=6.6 and 11 Hz), 3.23 (2H, s), 2.98–2.20 (7H, m), 1.88 (2H, m), 1.54 (2H, m), 1.48–1.15 (8H, m), 0.89 (3H, t, J=6.4 Hz).

Example 2(o)

11α,15α-dihydroxy-9-oxo-16β-methyl-3,7-dithiaprost-13E-enoic acid

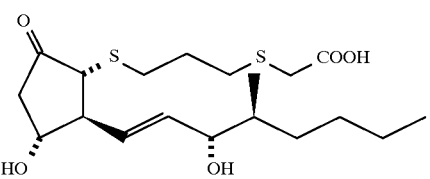

TLC: Rf 0.53, 0.42 (EtOAc/AcOH, 20:1);

NMR: δ5.85–5.60 (2H, m), 4.5–4.4 and 4.2–4.0 (2H, m), 4.6–3.8 (3H, br), 3.22 (2H, s), 3.45–3.40 and 3.1–2.2 (8H, m), 2.0–1.8 (2H, m), 1.7–1.1 (7H, m), 1.0–0.8 6H, m).

Example 2(p)

11α,15α-dihydroxy-9-oxo-3,7-dithiaprost-13E,19-dienoic acid

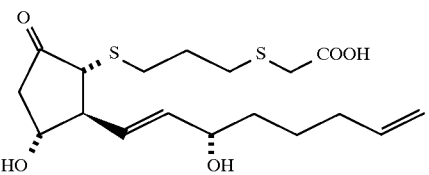

TLC: Rf 0.62, 0.56 (EtOAc/AcOH, 20/1);

NMR: δ5.88–5.48 (6H, m), 5.00 (2H, m), 4.42 and 4.15 (2H, each m), 3.40 and 3.02 (1H, each d, J=6.6 and J=11 Hz), 3.22 (2H, s), 3.06–2.28 (7H, m), 2.08 (2H, m), 1.86 (2H, m), 1.52 (4H, m).

Example 2(q)

11α,15α-dihydroxy-9-oxo-19,20-methano-3,7-dithiaprost-13E-enoic acid

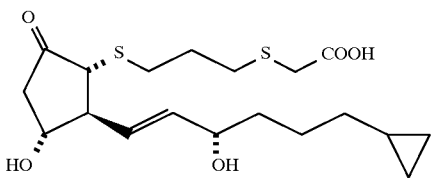

TLC: Rf 0.37, 0.19 (EtOAc/AcOH, 20/1);

NMR: δ5.74 (5H, m), 4.44 and 4.15 (2H, each m), 3.41 and 3.02 (1H, each d, J=6.8 Hz and J=11 Hz), 3.23 (2H, s), 2.98–2.19 (7H, m), 1.86 (2H, m), 1.73–1.10 (6H, m), 0.63 (1H, m), 0.40 (2H, m), 0.00 (2H, m).

Example 2(r)

11α,15α-dihydroxy-9-oxo-18-methyl-3,7-dithia-20-norprost-13E-enoic acid

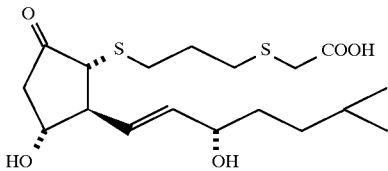

TLC: Rf 0.50, 0.27 (EtOAc/AcOH, 20/1);

NMR: δ5.68 (5H, m), 4.44 and 4.15 (2H, each m), 3.42 and 3.03 (1H, each d, J=6.6 Hz and J=11 Hz), 3.23 (2H, s), 2.98–2.20 (7H, m), 1.88 (2H, m), 1.57 (3H, m), 1.23 (2H, m), 0.90 (6H, d, J=6.6 Hz).

Example 2(s)

11α,15α-dihydroxy-9-oxo-16α-methyl-3,7-dithiaprost-13E-enoic acid

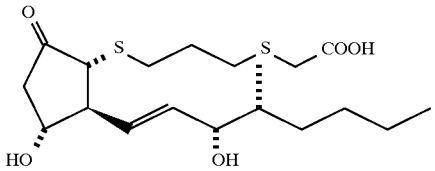

TLC: Rf 0.49, 0.39 (EtOAc/AcOH, 20:1);

NMR: δ5.9–5.6 (2H, m), 4.5–4.4 and 4.3–4.0 (2H, m), 4.7–3.9 (3H, br), 3.23 (2H, s), 3.45–3.40 and 2.9–2.2 (8H, m), 2.0–1.8 (2H, m), 1.7–1.0 (7H, m), 1.0–0.8 6H, m).

Example 2(t)

11α,15α-dihydroxy-9-oxo-16-cyclopentyl-3,7-dithia-17,18,19,20-tetranorprost-13E-enoic acid

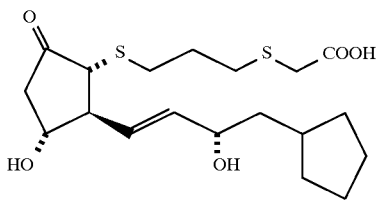

TLC: Rf 0.53, 0.37 (EtOAc/AcOH, 20/1);

NMR: δ5.76 (5H, m), 4.44 and 4.18 (2H, each m), 3.42 and 3.03 (1H, each d, J=6.8 Hz and J=11 Hz), 3.23 (2H, s), 2.96–2.20 (7H, m), 2.01–1.38 (11H, m), 1.13 (2H, m).

Example 2(u)

11α,15α-dihydroxy-9-oxo-16α-methyl-16-phenyl-3,7-dithia-20-norprost-13E-enoic acid

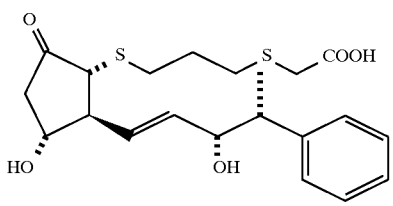

TLC: Rf 0.42, 0.32 (EtOAc/Hex/AcOH, 15:5:1);

NMR: δ7.4–7.2 (m, 5H), 5.71 (dd, J=15.6 Hz, 1H), 5.64 (dd, J=15, 8 Hz, 1H), 4.35 (t, J=6 Hz, 1H), 4.35 (t, J=6 Hz, 1H), 3.95 (q, J=8 Hz, 1H), 3.22 (s, 2H), 3.35–3.3 and 3.0–2.3 (m, 9H), 3.2–2.5 (br), 2.0–1.8 (m, 2H), 1.38 (d, J=6 Hz, 3H).

Formulation Example

The following components were admixed in conventional method and dried. Microcrystalline cellulose was added to the mixture to obtain the total weight 10 g. The resulting mixture was mixed sufficiently to make it homogeneous and then tabletted in conventional manner to give 100 tablets each containing 30 μg of the active ingredient.

a solution of 11α,15α-dihydroxy-9-oxo-3,7-dithiaprost-13E-enoic acid (3 mg) in ethanol 10 ml
magnesium stearate 100 mg
silicon dioxide 20 mg
talc 10 mg
carboxymethylcellulose calcium 200 mg
microcrystalline cellulose 5.0 g

We claim:
1. A 3,7-dithiaprostanoic acid derivative of the formula (I):

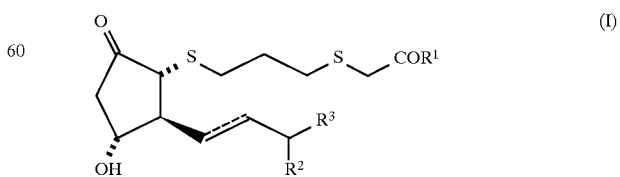

(wherein $R^1$ is hydroxy, C1–4 alkoxy or a group of the formula:

—NR⁶R⁷ wherein R⁶ and R⁷, independently, are hydrogen atom or C1–4 alkyl,

R² is hydrogen atom or hydroxy,

R³ is
(i) C1–8 alkyl, C2–8 alkenyl or C2–8 alkynyl,
(ii) phenyl or C3–7 cycloalkyl,
(iii) C1–8 alkyl, C2–8 alkenyl or C2–8 alkynyl substituted by phenyl or C3–7 cycloalkyl, with the proviso that, alkyl, alkenyl, alkynyl in (i) or (iii) may be substituted by one hydroxy group, when R² is hydrogen atom;

the symbol - - - is a double or single bond;

the formula including 8-epi equilibrium compound thereof);

a non-toxic salt thereof or a cyclodextrin clathrate thereof.

2. A compound according to claim 1, wherein R³ is C1–8 alkyl, C2–8 alkenyl or C2–8 alkynyl.

3. A compound according to claim 1, wherein R³ is phenyl or C3–7 cycloalkyl.

4. A compound according to claim 1, wherein R³ is C1–8 alkyl, C2–8 alkenyl or C2–8 alkynyl substituted by phenyl.

5. A compound according to claim 1, wherein R³ is C1–8 alkyl, C2–8 alkenyl or C2–8 alkynyl substituted by C3–7 cycloalkyl.

6. A compound according to claim 2, which is
11α,15α-dihydroxy-9-oxo-3,7-dithiaprost-13E-enoic acid,
11α,15α-dihydroxy-9-oxo-17β,20-dimethyl-3,7-dithiaprost-13E-enoic acid,
11α,15α-dihydroxy-9-oxo-17β,20-dimethyl-3,7-dithiaprost-13E-enoic acid,
11α,16β-dihydroxy-9-oxo-16α-methyl-3,7-dithiaprost-13E-enoic acid,
11α,15α-dihydroxy-9-oxo-3,7-dithiaprostanoic acid,
11α,15α-dihydroxy-9-oxo-3,7-dithiaprost-13E,17Z-dienoic acid
11α,15α-dihydroxy-9-oxo-15β-methyl-3,7-dithiaprost-13E-enoic acid,
11α,15α-dihydroxy-9-oxo-17-ethyl-3,7-dithia-20-norprost-13E-enoic acid,
11α,15α-dihydroxy-9-oxo-3,7-dithia-20-norprost-13E-enoic acid,
11α,15α-dihydroxy-9-oxo-3,7-dithia-20-homoprost-13E-enoic acid,
11α,15α-dihydroxy-9-oxo-16β-methyl-3,7-dithiaprost-13E-enoic acid,
11α,15α-dihydroxy-9-oxo-3,7-dithiaprost-13E,19-dienoic acid,
11α,15α-dihydroxy-9-oxo-18-methyl-3,7-dithia-20-norprost-13E-enoic acid or
11α,15α-dihydroxy-9-oxo-16α-methyl-3,7-dithiaprost-13E-enoic acid
or methyl ester thereof.

7. A compound according to claim 3, which is
11α,15α-dihydroxy-9-oxo-15-cyclohexyl-3,7-dithia-16,17,18,19,20-pentanorprost-13E-enoic acid or
11α,15α-dihydroxy-9-oxo-15-cyclopentyl-3,7-dithia-16,17,18,19,20-pentanorprost-13E-enoic acid or methyl ester thereof.

8. A compound according to claim 4, which is
11α,15α-dihydroxy-9-oxo-16-phenyl-17,18,19,20-tetranor-3,7-dithiaprost-13E-enoic acid,
11α,15α-dihydroxy-9-oxo-17-phenyl-18,19,20-trinor-3,7-dithiaprost-13E-enoic acid or
11α,15α-dihydroxy-9-oxo-16α-methyl-16-phenyl-3,7-dithia-20-norprost-13E-enoic acid or methyl ester thereof.

9. A compound according to claim 5, which is
11α,15α-dihydroxy-9-oxo-16-cyclohexyl-3,7-dithia-17,18,19,20-tetranorprost-13E-enoic acid,
11α,15α-dihydroxy-9-oxo-19,20-methano-3,7-dithiaprost-13E-enoic acid or
11α,15α-dihydroxy-9-oxo-16-cyclopentyl-3,7-dithia-17,18,19,20-tetranorprost-13E-enoic acid or methyl ester thereof.

10. An intermediate of the formula (II):

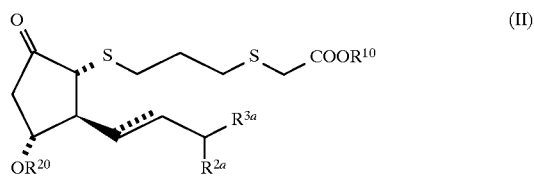

(II)

(wherein R²ᵃ is hydrogen atom or hydroxy protected by a protecting group which is eliminated under an acidic condition, R²⁰ is a protecting group which is eliminated under an acidic condition, R³ᵃ is (I) C1–8 alkyl, C2–8 alkenyl or C2–8 alkynyl, (ii) phenyl or C3–7 cycloalkyl, (iii) C1–8 alkyl, C2–8 alkenyl or C2–8 alkynyl which are substituted by phenyl or C3–7 cycloalkyl (with the proviso that when R²ᵃ is hydrogen, alkyl, alkenyl and alkynyl groups in (I) or (iii) may be substituted by one hydroxy protected by a protecting group which is eliminated under an acidic condition);

the symbol:

is a double or single bond).

11. A pharmaceutical composition with comprises, as active ingredient, a compound of the formula (I) depicted in claim 1 or a non-toxic salt thereof or a cyclodextrin clathrate thereof, with a pharmaceutical carrier or coating.

12. A method for the treatment and/or prevention in mammals, of immunologic diseases selected from the group consisting of autoimmune diseases, immunological deficiency diseases and organ transplantation; asthma, abnormal bone formation, neuronal cell death, liver damage, nephritis, hypertension or myocardiac ischemia, which comprises administering to a patient an effective amount of a compound of the formula (I) depicted in claim 1 or a non-toxic salts thereof or a cyclodextrin clathrate thereof.

* * * * *